(12) United States Patent
Pessel et al.

(10) Patent No.: US 12,084,398 B2
(45) Date of Patent: Sep. 10, 2024

(54) PROCESS FOR PREPARING A SURFACTANT COMPOSITION BASED ON A GLYCINE BETAINE ESTER SALT, AND COMPOSITION THUS OBTAINED

(71) Applicant: SURFACTGREEN, Compiegne (FR)

(72) Inventors: Freddy Pessel, Rennes (FR); Francis Galle, Rennes (FR); Pierre-Yves Divet, Neuilly-sur-Seine (FR); Xavier Roussel, Le Mans (FR)

(73) Assignee: SURFACTGREEN, Compiegne (FR)

( * ) Notice: Subject to any disclaimer, the term of this patent is extended or adjusted under 35 U.S.C. 154(b) by 675 days.

(21) Appl. No.: 17/296,999

(22) PCT Filed: Nov. 25, 2019

(86) PCT No.: PCT/FR2019/052801
§ 371 (c)(1),
(2) Date: May 26, 2021

(87) PCT Pub. No.: WO2020/109710
PCT Pub. Date: Jun. 4, 2020

(65) Prior Publication Data
US 2022/0024855 A1    Jan. 27, 2022

(30) Foreign Application Priority Data

Nov. 27, 2018  (FR) ...................... 1871892

(51) Int. Cl.
*C07C 227/18* (2006.01)
*A01N 25/30* (2006.01)
*A61K 8/41* (2006.01)

(52) U.S. Cl.
CPC ............ *C07C 227/18* (2013.01); *A01N 25/30* (2013.01); *A61K 8/416* (2013.01)

(58) Field of Classification Search
CPC ........ A01N 25/30; A01N 37/44; A61K 8/416; A61K 8/44; A61Q 19/10; A61Q 5/02; A61Q 5/12; C07C 227/18; C07C 229/12; C11D 1/90; C11D 3/48
See application file for complete search history.

(56) References Cited

U.S. PATENT DOCUMENTS

| | | |
|---|---|---|
| 7,829,521 B2 | 11/2010 | Antoine et al. |
| 9,956,154 B2 | 5/2018 | Perusse et al. |
| 11,224,220 B2 | 1/2022 | Pessel et al. |

FOREIGN PATENT DOCUMENTS

| | | |
|---|---|---|
| WO | WO 2009/150369 | 12/2009 |
| WO | WO 2013/188508 | 12/2013 |
| WO | WO 2015/003968 | * 1/2015 |
| WO | WO 2015/078890 | 6/2015 |

OTHER PUBLICATIONS

Goursaud, F. et al. "Glycine betaine as a renewable raw material to "greener" new cationic surfactants" *Green Chemistry*, 2008, pp. 310-320, vol. 10.
Written Opinion in International Application No. PCT/FR2019/052801, May 19, 2020, pp. 1-7.

* cited by examiner

*Primary Examiner* — Yevgeny Valenrod
*Assistant Examiner* — Blaine G Doletski
(74) *Attorney, Agent, or Firm* — SALIWANCHIK, LLOYD & EISENSCHENK

(57) ABSTRACT

The present invention relates to a process for preparing a surfactant composition based on glycine betaine ester salt, and to the composition thus obtained. The invention also relates to the uses of said composition. A subject of the invention is also a product comprising the abovementioned composition.

15 Claims, 1 Drawing Sheet

PROCESS FOR PREPARING A SURFACTANT COMPOSITION BASED ON A GLYCINE BETAINE ESTER SALT, AND COMPOSITION THUS OBTAINED

CROSS-REFERENCE TO RELATED APPLICATION

This application is the U.S. national stage application of International Patent Application No. PCT/FR2019/052801, filed Nov. 25, 2019.

SUBJECT OF THE INVENTION

The present invention relates to a process for preparing a surfactant composition based on glycine betaine ester salt, and also to the composition thus obtained. It also relates to the uses of said composition. A further subject of the invention is a product comprising the abovementioned composition.

BACKGROUND OF THE INVENTION

Surfactants are raw materials which are essential for the manufacture of a variety of products. Among these products, cationic surfactants clearly represent a market which is not as extensive as that of nonionic or anionic surfactants; however, they are valuable in a host of applications, notably in the manufacture of detergent and cosmetic products, and also for water treatment.

Due to their toxicity, some surfactants such as dimethyldialkylammonium salts, present in most fabric softeners, have seen their use reduced or even stopped in some European countries such as Germany and the Netherlands. Under ecological pressure, surfactant producers have to offer products that pollute less, are more biodegradable and present the lowest possible ecotoxicity. Consumer desire for products that are as natural as possible adds to these environmental constraints.

In this context, glycine betaine, a cheap natural substance, is a raw material of choice for the preparation of surfactants. Originating from sugar beet molasses and obtained after extraction of sucrose, it is currently a byproduct of the sugar industry. Grafting fatty alcohols and amines onto glycine betaine affords access to cationic amphiphilic molecules without the conventional quaternization step of a tertiary amine using methylating agents which are generally toxic.

U.S. Pat. No. 7,829,521 thus proposes glycine betaine esters obtained by reaction of glycine betaine with at least two equivalents of a sulfonic acid, such as methanesulfonic acid, and an alcohol comprising at least 18 carbon atoms. The cationic surfactants thus obtained are present as a mixture with the residual reagents and this mixture may optionally be enriched in glycine betaine ester by treatment using an organic solvent and/or purified on a silica gel column. It is thus possible to obtain an octadecyl or octadecenyl ester of glycine betaine in a yield of about 70% or 85%, respectively. These products have a surface tension of about 37 mN/m and are more particularly aimed at cosmetic applications.

Other similar surfactants and also surfactants having a shorter chain (lauryl ester) are present in the publication by F. Goursaud et al. in *Green Chem.*, 2008, 10, 310-320. These surfactants are also prepared in the presence of an amount of methanesulfonic acid of at least two equivalents relative to the amount of glycine betaine used, which is described as being necessary to obtain a satisfactory yield (at least 70%). The surface tension of the esters obtained after purification is once again very high (from 32 to 37 mN/m).

The lauryl ester of glycine betaine is also described, alone or as a mixture with the corresponding myristyl ester, in patent application WO 2013/188508. In said application, it is shown (Table 5) that the raw reaction mixture has a lower surface tension than that of pure glycine betaine ester, which enables its use in household detergents. This reaction mixture contains in all cases less than 65% by weight of glycine betaine ester and/or more than 20% by weight of residual sulfonic acid (Table 4). However, the present inventors have shown that adjusting these two parameters enabled a further decrease in the surface tension of these mixtures.

For its part, WO 2015/078890 discloses a surfactant composition obtained by reacting, in a first step, glycine betaine with an alcohol of formula R1-OH containing from 1 to 6 carbon atoms, and then with an alcohol of formula R2-OH having a longer chain, in the presence of a sugar hemiacetal. This two-step process results in a complex surfactant composition. Moreover, WO 2015/003968 describes deodorant active agents consisting of glycine betaine ester salts, which may be prepared using a process involving the reaction of glycine betaine with an alcohol R—OH in which R is a C2-C22 alkyl, in the presence of an excess of acid, at a temperature of between 60 and 160° C. Only Examples 1 and 2 relate to C8-C22 esters, which may thus possess surfactant properties. In these examples, the reaction temperature is 140° C. and the acid content is less than 1.5 equivalents. The glycine betaine esters are obtained in a yield not exceeding 44%.

After extensive research, the inventors have thus developed a modified process for preparing glycine betaine ester salts, in which the esterification reaction is performed in the presence of a reduced amount of acid and at a higher temperature than the prior art processes described above. This process makes it possible to obtain, in only one step, surfactant compositions having lower surface tensions and optionally a higher proportion of glycine betaine ester compared to the surfactant compositions described in the prior art, without substantially affecting the reaction yield. This process may further be implemented within a shorter time period and does not require any step for purification of the obtained product.

The synthetic process implemented according to the invention is simple, effective, environmentally friendly, without any solvent or pollutant waste, and easily transposable to an industrial scale, making it possible to obtain, in a reproducible manner, a particularly efficient surfactant composition.

SUMMARY OF THE INVENTION

One subject of the invention is a process for preparing a surfactant composition, comprising the successive steps consisting in:
(1) reacting glycine betaine or a salt thereof with a saturated or unsaturated, linear or branched fatty alcohol containing from 8 to 24 carbon atoms, in the presence of an organic or inorganic acid;
(2) cooling the reaction medium to a temperature of from 20 to 90° C.; and
(3) collecting the surfactant composition thus obtained, characterized in that the organic or inorganic acid represents from 1.5 to 2.0 molar equivalents relative to the number of moles of glycine betaine and in that the reaction is performed at a temperature of from 150 to 180° C.

A subject of the invention is also the surfactant composition obtained according to said process, containing the following constituents:

(a) from 65% to 85% by weight, preferably from 70% to 80% by weight, of a glycine betaine ester salt,
(b) from 1% to 20% by weight, for example from 1% to 9% by weight or from 10% to 20% by weight, of a fatty alcohol,
(c) from 1% to 20% by weight, for example from 5% to 15% by weight, of an organic or inorganic acid, and
(d) from 1% to 20% by weight, for example from 2% to 15% by weight, of a glycine betaine salt, relative to the total weight of these four constituents.

A subject of the invention is also the use of the abovementioned surfactant composition as a wetting agent, particle dispersant, corrosion inhibitor, solubilizing agent, antistatic and/or disentangling agent and/or for improving the effect and/or the persistence of insecticidal substances and/or for improving the disinfecting power and/or the persistence of the disinfecting effect of antimicrobial substances.

A subject of the invention is also the use of said composition for manufacturing plastics or products intended for:

treating and/or cleansing the body, plants or hard surfaces, in particular cosmetic products, products for washing vehicles, household products, industrial cleaning products, fiber sizing products and plant protection products;
treating water;
road surfacing; or
extracting petroleum.

A subject of the invention is also a product comprising the abovementioned composition and at least one constituent chosen from: (a) anionic surfactants, nonionic surfactants and mixtures thereof, (b) antimicrobial agents, (c) insecticides, and mixtures thereof.

Beside its low surface tension, the surfactant composition obtained according to the invention has the advantage of being biodegradable (according to the standard OECD 301), with a low toxicity toward the environment (according to the standards OECD 201 and 202) and toward human beings.

DETAILED DESCRIPTION

Process

The surfactant composition according to the invention may be prepared according to a process of esterification of glycine betaine, or trimethylglycine. The glycine betaine may be of plant or synthetic origin. A prior protonation using an organic or inorganic acid, given that glycine betaine is in zwitterionic form (presence of a carboxylate function), is required. The acid may notably be chosen from inorganic acids such as hydrochloric acid, sulfuric acid, perhydrohalic acids, such as perchloric acid, and mixtures thereof. As a variant, it may be chosen from organic acids, such as alkylsulfuric acids, for example decyl or laurylsulfuric acid; arylsulfonic acids, such as benzenesulfonic acid, para-toluenesulfonic acid; alkylsulfonic acids, such as triflic acid, methanesulfonic acid, ethanesulfonic acid, decylsulfonic acid, laurylsulfonic acid, camphorsulfonic acid; sulfosuccinic acid; and mixtures thereof. Lewis acids may also be used. Preferably, it is an alkylsulfonic acid and in particular methanesulfonic acid, given that it is readily biodegradable.

During esterification, the acid function of the salified betaine is reacted with a fatty alcohol, so as to produce a glycine betaine ester in salt form. The term "fatty alcohol" means a saturated or unsaturated, linear or branched (preferably linear) alcohol comprising from 8 to 24 carbon atoms. Examples of such fatty alcohols may be chosen from the group consisting of: capryl alcohol (C8:0), decyl alcohol (C10:0), undecyl alcohol (C11:0), lauryl alcohol (C12:0), myristyl alcohol (C14:0), cetyl alcohol (C16:0), palmitoleyl alcohol (C16:1), stearyl alcohol (C18:0), oleyl alcohol (C18:1), linoleyl alcohol (C18:2), linolenyl alcohol (C18:3), arachidyl alcohol (C20:0), arachidonyl alcohol (C20:4), behenyl alcohol (C22:0), 2-butyloctanol, 2-hexyldecanol, 2-octyldodecanol, 2-decyltetradecanol and mixtures thereof. Useful fatty alcohol mixtures may be produced from one or more plant oils and notably from soybean oil, olive oil, sunflower oil, corn oil, palm oil, coconut kernel oil, cottonseed oil, linseed oil, wheat germ oil, safflower oil or rapeseed oil, for example.

The esterification reaction generally takes place in the absence of solvent. The water produced during the reaction moreover contributes toward solubilizing the glycine betaine in the reaction mixture.

For the implementation of this reaction, from 0.8 to 2 equivalents, for example from 0.9 to 1.0 equivalent, or as a variant, from 1.1 to 1.8 equivalents, preferentially in this case from 1.2 to 1.6 equivalents and better still from 1.3 to 1.5 equivalents of fatty alcohol may be used. In any case, from 1.5 to 2.0 equivalents, for example from 1.5 to 1.9 equivalents, and preferentially from 1.5 to 1.7 molar equivalents of organic or inorganic acid per 1 equivalent of glycine betaine are used. The esterification is performed at a temperature of from 150 to 180° C. In a preferred embodiment of the invention, the glycine betaine, the fatty alcohol and the organic or inorganic acid are mixed at a temperature of from 160 to 180° C., for example 170° C., and the temperature of the mixture is then decreased by 10 to 20° C., to 140-160° C., for example to 150° C., before the start of the reaction. The reaction may be performed under atmospheric pressure or preferably under reduced pressure, for example at a pressure of from 10 to 600 mbar. Generally, the pressure will be proportionately smaller the longer the chain length of the fatty alcohol involved. In any case, a person skilled in the art will know how to adjust the chosen pressure so as to remove the water formed during the reaction and to shift the equilibrium toward the ester formation. The reaction mixture is then cooled to a temperature of from 20 to 90° C.

The surfactant composition thus obtained is then collected, said composition containing at least 65% by weight, generally from 65% to 85% by weight, for example from 70% to 80% by weight, of at least one glycine betaine ester salt of formula $X^{n-}[(CH_3)_3N^+—CH_2—COOR]_n$ in which: X is an organic or inorganic anion, R is an alkyl radical corresponding to the fatty alcohol R—OH used in the esterification reaction, and n is 1 or 2.

The anion X derives from the acid XH described previously and may thus be in particular chloride, sulfate, perchlorate, an alkylsulfate ion, notably decylsulfate or laurylsulfate, an arylsulfonate ion, notably benzenesulfonate, para-toluenesulfonate, an alkylsulfonate ion, notably triflate, methanesulfonate, ethanesulfonate, decylsulfonate, laurylsulfonate, camphorsulfonate, or a sulfosuccinate ion. According to the invention, it is preferred for X to be chosen from alkylsulfonates and arylsulfonates, in particular from methanesulfonate, triflate, para-toluenesulfonate and camphorsulfonate ions. Advantageously, it is a methanesulfonate ion.

As regards the radical R, it may be chosen from octyl (C8:0), decyl (C10:0), undecyl (C11:0), lauryl (C12:0), myristyl (C14:0), cetyl (C16:0), palmitoleyl (C16:1), stearyl (C18:0), oleyl (C18:1), linoleyl (C18:2), linolenyl (C18:3), arachidyl (C20:0), arachidonyl (C20:4), behenyl (C22:0), 2-butyloctyl, 2-hexyldecyl, 2-octyldodecyl and 2-decyltetradecyle groups.

Naturally, it is understood that, in the case where several fatty alcohols are used in the esterification reaction, the surfactant composition obtained according to the invention will comprise several glycine betaine ester salts. The expression "glycine betaine ester salt" must thus be understood, in the context of the present description and unless indicated otherwise, as meaning one or more of said salts.

More precisely, the surfactant composition obtained according to the invention contains:
- (a) from 65% to 85% by weight, preferably from 70% to 80% by weight, of a glycine betaine ester salt,
- (b) from 1% to 20% by weight, for example from 1% to 9% by weight or from 10% to 20% by weight, of a fatty alcohol,
- (c) from 1% to 20% by weight, for example from 5% to 15% by weight, of an organic or inorganic acid, and
- (d) from 1% to 20% by weight, for example from 2% to 15% by weight, of a glycine betaine salt, relative to the total weight of these four constituents.

Advantageously, said constituents represent a total of from 90% to 100%, and preferably from 95% to 100% of the weight of the composition. The remaining constituents of the composition may in particular consist of a fatty alcohol ether of formula R—O—R, in which R is as defined previously.

The surfactant composition obtained according to the invention may in particular comprise the above constituents in the following proportions:
- in the case where the fatty alcohol is lauryl alcohol: from 70% to 80% by weight of glycine betaine lauryl ester salt, from 0.1% to 15% by weight of lauryl alcohol, from 10% to 15% by weight of an organic or inorganic acid and from 1% to 10% by weight of glycine betaine salt;
- in the case where the fatty alcohol is a mixture of lauryl and myristyl alcohols: from 65% to 75%, preferably from 70% to 75% by weight of glycine betaine lauryl and myristyl esters salts, from 1% to 20%, for example from 1% to 9% by weight or from 10% to 20% by weight, of lauryl and myristyl alcohols, from 10% to 20%, preferably from 10% to 15% by weight, of an organic or inorganic acid and from 1% to 15% by weight of glycine betaine salt;
- in the case where the fatty alcohol is oleyl alcohol: from 70% to 80%, preferably from 70% to 75% by weight of glycine betaine oleyl ester salt, from 1% to 20%, for example from 5% to 10% by weight or from 11% to 20% by weight, of oleyl alcohol, from 5% to 15% by weight of an organic or inorganic acid and from 1% to 15% by weight of glycine betaine salt.

It has been observed that the use of alcohol in deficit relative to the glycine betaine, in the process according to the invention, makes it possible to obtain surfactant compositions which, besides their lower surface tension relative to the prior art compositions, have better water solubility. The aqueous surfactant solutions obtained from said surfactant compositions are thus more fluid and more transparent, which is an advantage when the solution is to be sprayed or impregnated on a fibrous support such as wipes.

Uses

The surfactant composition obtained according to the invention has a surface tension value of less than 30 mN/m, or even of less than 25 mN/m and generally of greater than 20 mN/m, measured according to the standard NF EN 14370.

Its use may thus be envisaged in various applications as a wetting agent, particle dispersant, corrosion inhibitor, solubilizing agent, antistatic, disentangling agent and/or for improving the effect and/or the persistence of insecticidal substances and/or for improving the disinfecting power of antimicrobial substances. It may in particular be used for manufacturing plastics or different products, notably for:
- treating and/or cleansing the body, plants, textiles or hard surfaces, in particular cosmetic products, such as shampoos, conditioners, liquid soaps, bubble baths and shower gels; products for washing vehicles such as automobiles, trucks, trains, buses or aircraft; household products such as detergents for windows, wall surfaces, floorings or tableware; maintenance products for textiles; industrial cleaning products; fiber sizing products; plant protection products; pigmented products such as paints or varnishes;
- treating water;
- road surfacing, for example bituminous emulsions;
- extracting petroleum.

In the case of water treatment, the composition according to the invention makes it possible to peel off biofilms without compromising the efficiency of ion-exchange resins, as opposed to conventional cationic surfactants which moreover have a significant impact on the environment due to their absence of biodegradability or their slower biodegradability. This ability to peel off biofilms may also advantageously be exploited in petroleum extraction processes.

In cosmetic applications, the composition according to the invention is compatible with conventional anionic surfactants and makes it possible to improve the creamy nature of the foam they generate. It also protects iron-based aerosol devices against corrosion. It has also been shown that the composition according to the invention makes it possible to reduce the static electricity of hair and facilitates its disentangling. The solubilizing power of the composition according to the invention further makes it possible to envisage its use for solubilizing fragrances or essential oils, and its dispersing capacity may enable the dispersion of pigments present in cosmetic compositions.

In the manufacture of plastics, the composition according to the invention makes it possible to impart electrostatic properties to the plastic surface, without affecting its recyclability given its biobased nature.

When it is used in the manufacture of plant protection products, the composition according to the invention makes it possible to improve the persistence of the active agents and the water resistance of products such as herbicides, pesticides or plant growth modifiers, which may thus be used in a lower amount. Said composition may then be added, as a form diluted to 25% in water, at 0.4% by weight, in a product containing an acidic medium, for example.

The composition according to the invention may moreover be used in a process for the extraction, storage, stockpiling or refining of petroleum, so as to limit equipment corrosion. In this application, it may be added to petroleum in an amount of from 500 to 1000 ppm, for example.

A subject of the invention is also a product, for example chosen from those described above, comprising a composition according to the invention and at least one compound chosen from: anionic surfactants, nonionic surfactants, antimicrobial agents and mixtures thereof. Examples of anionic surfactants are: sulfate salts of ethoxylated fatty alcohols, sulfosuccinates, sarcosinates, alkyl- and dialkylphosphates, fatty acid soaps and mixtures thereof. Nonionic surfactants may be chosen, for example, from: fatty acid esters of polyols, such as optionally polyethoxylated fatty acid esters of glycerol, optionally polyethoxylated fatty acid esters of sorbitan, polyoxyethylenated fatty acid esters, fatty acid esters of sucrose such as sucrose stearate, polyoxyethylenated fatty alcohol ethers, fatty alcohol ethers of sugars, notably alkylpolyglucosides (APG), modified polysiloxane polyethers, and mixtures thereof. The antimicrobial agents may be chosen from quaternary ammoniums, aldehydes (such as glutaraldehyde and formaldehyde), ethanol, halo derivatives, oxidants, phenolic compounds, parabens, isothiazolones (or isothiazolinones), benzoates, imidazoline, hydantoin, guanidine, organic acids such as lactic acid, and mixtures thereof. The insecticidal substances may be chosen from organophosphorus agents (such as acephate, chlorpyrifos or bromophos), nicotinoids, pyrethroids (such as permethrin, bifenthrin or fenvalerate), monoterpenes (such as p-menthane-3,8-diol), organohalogen compounds (such as lindane, dicofol or toxaphene), N,N-diethyl-3-methylbenzamide, pyrethrum derivatives (such as pyrethrin I, pyrethrin II or jasmolin I), sulfones, sulfonates, formamidines, benzoylureas, rotenones, alkaloids, quassin, ryanidone, aconitine, geraniol and mixtures thereof.

Said product is advantageously in the form of an aqueous solution or an aqueous gel. As a variant, it may be in the form of an oil-in-water or water-in-oil emulsion, or even as a paste. In any case, the aqueous phase present in said product advantageously has a pH of from 1 to 8, notably from 1 to 5. Said product may be packaged in any device suitable for the envisaged use and notably in a pump bottle, a tube, a jar, an aerosol spray device or a wipe.

Advantageously, it contains from 0.1% to 25% by weight, for example from 1% to 10% by weight, of the surfactant composition according to the invention.

The product according to the invention may also comprise, in addition to the abovementioned antimicrobial agents, insecticides and surfactants, and according to the envisaged application, at least one ingredient chosen from: plant protection or cosmetic active agents, enzymes, chelating agents, thickeners, fatty substances (oils, waxes and/or pastes), fillers, preserving agents, pigments and colorants, antioxidants, optical brighteners, and mixtures thereof.

FIGURES

EXAMPLES

Figure 1:
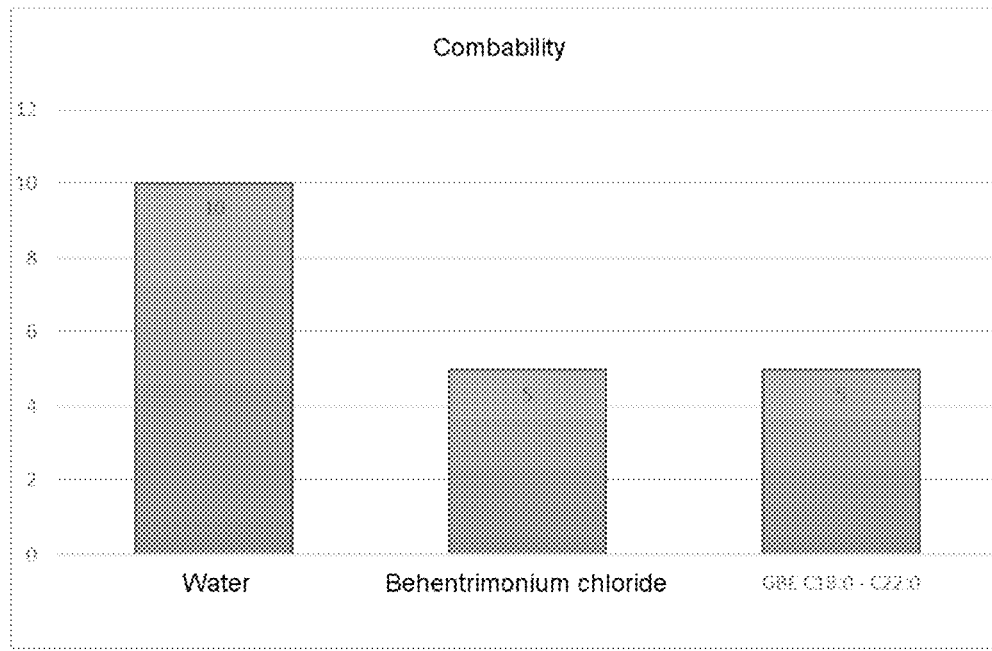
FIG. 1 illustrates the combability of a lock of hair treated with water, a composition containing a reference surfactant, and the same composition containing a mixture of glycine betaine ester salts according to the invention, respectively.

The invention will be better understood in the light of the following examples, which are given for illustrative purposes only and are not intended to limit the scope of the invention, defined by the appended claims.

Example 1: Synthesis of a Surfactant Composition According to the Invention

Glycine betaine (1.0 eq.) and a fatty alcohol are introduced into a reactor. The nominal temperature for the mixture is set at 170° C. and the pressure is reduced to a value of from 10 to 600 mbar, according to the alcohol used. After reaching the nominal pressure and temperature, a 70% methanesulfonic acid solution (1.6 eq.) is added to the reaction mixture. Once the addition is finished, the nominal temperature is brought down to 150° C. and the pressure is maintained at a value of from 10 to 600 mbar, according to the alcohol used. Four hours after the start of the acid introduction, the reaction mixture is allowed to cool down to 80° C., and the product is then collected, cooled down to room temperature, and the reaction yield is determined by $^1$H NMR.

This process was performed using various fatty alcohols. Said alcohols were used either in excess (1.4 equivalents) or in deficit (0.9 equivalent) relative to the glycine betaine.

The surface tension measurements were performed according to the standard NF EN 14370, using a Krüss tensiometer equipped with a horizontally suspended platinum ring. Before each measurement, the ring is thoroughly cleaned and flame-dried. The sample cup is a conical PTFE container placed in a temperature-controlled enclosure at 25° C. The sample is prepared using Milli-Q water and continuously stirred with a magnetic bar before each measurement.

The products obtained had the following mass composition:

| | Excess alcohol | | | Deficit alcohol | | |
|---|---|---|---|---|---|---|
| Constituent | R = C12:0 | R = C12:0/C14:0 | R = C18:1 | R = C12:0 | R = C12:0/C14:0 | R = C18:1 |
| Betainate alkyl mesylate | 74% | 72% | 72% | 77% | 70% | 72% |
| Residual fatty alcohol | 11% | 13% | 16% | 1% | 4% | 6% |
| Residual methanesulfonic acid | 12% | 11% | 9% | 14% | 14% | 12% |
| Residual glycine betaine mesylate | 3% | 4% | 3% | 8% | 12% | 10% |
| Yield[(1)] | 93% | 90% | 92% | 93% | 86% | 83% |
| CMC surface tension (mN/m) | 21 at pH 3 | 21.8 at pH 3 | 29 at pH 3 | 21 at pH 3 | 21.8 at pH 3 | 29 at pH 3 |

| | Excess alcohol | |
|---|---|---|
| Constituent | R = 2-hexyldecyl | R = 2-octyldodecyl |
| Betainate alkyl mesylate | 69% | 73% |
| Residual fatty alcohol | 17% | 16% |

-continued

| | | |
|---|---|---|
| Residual methanesulfonic acid | 11% | 10% |
| Residual glycine betaine mesylate | 3% | 1% |
| Yield | 93% | 96% |
| CMC surface tension (mN/m) | 26.0 mN/m at pH = 3 | 25.9 mN/m at pH = 3 |

| Constituent | Excess alcohol R = C10:0 | Deficit alcohol R = C10:0 |
|---|---|---|
| Betainate alkyl mesylate | 71% | 75% |
| Residual fatty alcohol | 14% | 2% |
| Residual methanesulfonic acid | 12% | 14% |
| Residual glycine betaine mesylate | 4% | 9% |
| Yield | 92% | 91% |
| CMC surface tension (mN/m) | 23.0 mN/m at pH = 3 | 26.3 mN/m at pH = 3 |

[1]Calculated relative to the glycine betaine (excess alcohol) or the fatty alcohol (deficit alcohol)

A reaction yield which is always greater than or equal to 75% is observed. Moreover, for esters containing at least 12 carbon atoms, the CMC surface tension of the compositions obtained according to the invention does not depend on the amount of fatty alcohol used, which makes it possible to use a lower amount of alcohol. As the latter has a significant impact on the process cost, this is an undeniable economic advantage of the process according to the invention. Moreover, as the residual fatty alcohol reduces the water solubility of surfactant compositions, using deficit alcohol in the process according to the invention makes it possible to obtain, from said surfactant compositions, aqueous surfactant solutions which are more fluid and transparent.

In comparison, the products described in WO 2013/188508 and U.S. Pat. No. 7,829,521 and in the publication by Goursaud et al. (*Green Chem.*, 2008, 10, 310-320) had the following features:

| | R = C12:0 | R = C12:0/C14:0 | R = C18:1 | | R = C18:0 | |
|---|---|---|---|---|---|---|
| Constituent | Goursaud WO'508 | WO'508 | US'521 | Goursaud | US'521 | Goursaud |
| Yield | 95% — | — | 85% | 85% | 80% | 70% |
| CMC surface tension (mN/m) | 32  27 | 24 | 36.6 | 37 | 37 | 37 |

Said products were obtained, according to said documents, by reaction of glycine betaine with from 1.0 to 1.5 equivalents of alcohol in the presence of from 2 to 3 equivalents of methanesulfonic acid, at a temperature of from 120 to 140° C. and under a pressure of from 30 to 100 mbar, for a reaction time of from 6 to 8 h. The products obtained by Goursaud and in US'521 were moreover purified.

The products according to the invention, employing a lower amount of methanesulfonic acid and a higher temperature, thus appear to have, in a totally unexpected manner, improved properties which make it possible to use them in various applications. Moreover, said products are obtained in a yield similar (greater than 80%) to those of the prior art but in a shorter time, which is undeniably advantageous from an industrial viewpoint.

Example 2: Disentangling Test

A comparative test of disentangling a lock of hair was performed using a fatty alcohol emulsion in water, containing either a mixture of glycine betaine C18 to C22 ester salts according to the invention, or behentrimonium chloride (Varisoft® BT 85 from Evonik). Moreover, water was used as a control. To do this, two locks of hair were washed beforehand using a lauryl ether sulfate solution, rinsed with water and then dried, before being rubbed 15 times in the palm of the hand so as to entangle the hair. 1 g of each product was then applied onto one of the two wet locks which was then massaged eight times along its entire length to ensure proper distribution of the product. After 3 minutes of leave-on time, the locks were rinsed with tap water and then hand-dried. After being arranged on a flat surface, the number of comb strokes necessary to obtain a lock which could be combed without constraint was measured. This procedure was repeated three times per product, on three different locks. Only one test was performed using tap water.

The results of these tests are illustrated in FIG. 1. As revealed in this Figure, the glycine betaine ester salts according to the invention offer performance qualities equivalent to those of the reference surfactant. However, the glycine betaine derivatives have greater biodegradability than the reference surfactant, are 100% biobased and their synthesis process is more environmentally friendly.

Figure 2:
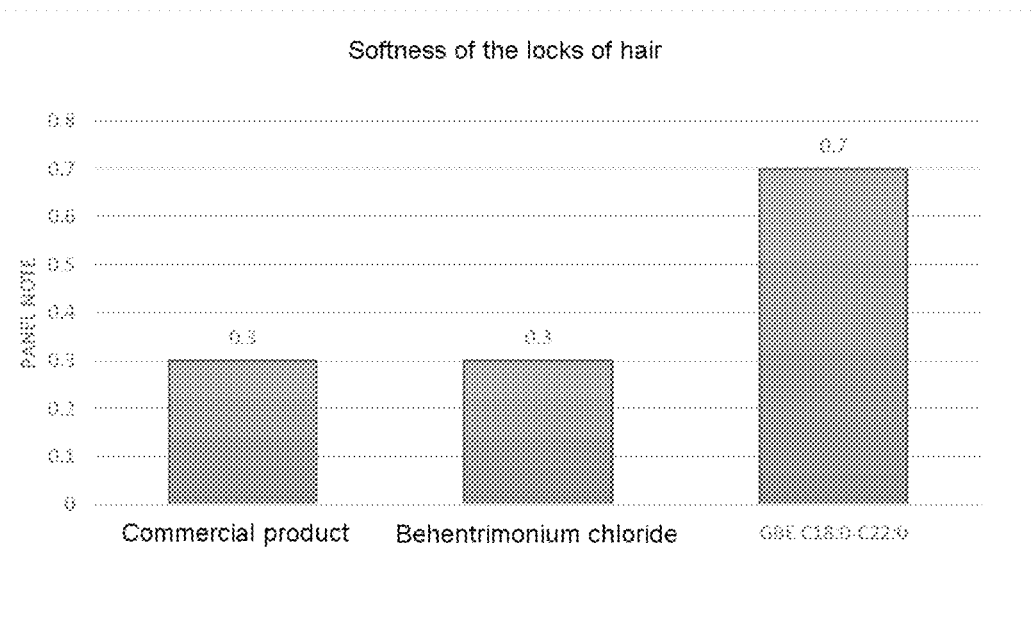
FIG. 2 is a diagram illustrating the softness of locks treated using a disentangling composition containing a reference surfactant or a mixture of glycine betaine ester salts according to the invention, in comparison with a commercial disentangling agent.

Sensory analysis of the softness of the locks thus obtained was then performed by three panel members, in comparison with a lock treated as above, but with a commercial disentangling agent (Elseve® Total Repair Rapid Restore). The results of this evaluation are presented in FIG. 2. As shown in this Figure, the locks obtained are perceived as being much softer than those treated with the reference surfactant and even with the commercial disentangling agent.

Example 3: Formulations

Several types of products may be prepared using the surfactant compositions according to the invention, based, respectively, on lauryl ester (GBE C12:0), myristyl ester (GBE C14:0), palmityl ester (GBE C16:0), stearyl ester (GBE C18:0), oleyl ester (GBE C18:1), behenyl ester (GBE C22:0), 2-octyldodecyl ester (GBE C20R:0) or mixtures thereof.

Household Detergent

| | |
|---|---|
| 80% lactic acid | 2.00% |
| GBE C12:0/C14:0 | 0.40% |
| Hydroxyethyl cellulose | 0.30% |
| Chelating agent | 0.20% |
| Fragrance | 0.20% |
| Colorant | 0.01% |
| Deionized water | qs 100.00% |

Concentrated Softener

| | |
|---|---|
| GBE C20R:0 | 15.00% |
| 25% calcium chloride | 1.50% |
| Fragrance | 0.70% |
| Colorant | 0.02% |
| Preserving agent | 0.10% |
| Water | qs 100.00% |

Toilet Product

| | |
|---|---|
| 85% phosphoric acid | 5.90% |
| 37% hydrochloric acid | 13.50% |
| GBE C12:0 | 3.00% |
| Fragrance | 0.20% |
| Colorant | 0.01% |
| Water | qs 100.00% |

Shampoo

| | |
|---|---|
| GBE C18:1 | 30.00% |
| Coconut kernel diethanolamide | 5.00% |
| Citric acid | qs pH 5 |
| Preserving agent | qs |
| Water | qs 100.00% |

Hair Conditioner

| | |
|---|---|
| GBE C16:0/C18:0 | 3.00% |
| Cetyl/stearyl alcohols | 5.00% |
| Sodium citrate | qs pH 2.5-3.0 |
| Fragrance | 0.25% |
| Colorant | 0.02% |
| Preserving agent | 0.01% |
| Water | qs 100.00% |

Hair Mask

| | |
|---|---|
| GBE C18:0/C22:0 | 3.00% |
| Cetyl/stearyl alcohols | 5.00% |
| Olive oil | 5.00% |
| Sodium citrate | qs pH 2.5-3.0 |
| Panthenol | 0.15% |
| Fragrance | 0.05% |
| Colorant | 0.02% |
| Preserving agent | 0.01% |
| Water | qs 100.00% |

Plant Protection Adjuvant (Emulsifiable Concentrate)

| | |
|---|---|
| GBE C12:0 | 6.00% |
| GBE C18:1 | 8.00% |
| Antifoam agent | 0.10% |
| Rapeseed methyl ester | qs 100.00% |

The invention claimed is:

1. A surfactant composition, which contains the following constituents:
   a) from 65% to 85% by weight of a glycine betaine ester salt,
   b) from 1% to 20% by weight of a fatty alcohol,
   c) from 1% to 20% by weight of an organic or inorganic acid, and
   d) from 1% to 20% by weight of a glycine betaine salt,
   relative to the total weight of these four constituents.

2. The composition according to claim 1, wherein said constituents represent a total of from 90% to 100% by weight of the composition.

3. The composition according to claim 1, which has a surface tension value of less than 30 mN/m measured according to the standard NF EN 14370.

4. An agent selected from the group consisting of a wetting agent, particle dispersant, corrosion inhibitor, solubilizing agent, antistatic and/or disentangling agent comprising the surfactant composition according to claim 1.

5. A product selected from the group consisting of: plastics and products intended for:
   treating and/or cleansing the body, plants or hard surfaces, cosmetic products, products for washing vehicles, household products, industrial cleaning products, fiber sizing products and plant protection products;
   treating water;
   road surfacing; or
   extracting petroleum,
   comprising the composition according to claim 1.

6. A product comprising the composition according to claim 1 and at least one constituent chosen from: (a) anionic surfactants, nonionic surfactants and mixtures thereof, (b) antimicrobial agents, (c) insecticides, and mixtures thereof.

7. An agent for improving the effect and/or the persistence of insecticidal substances and/or for improving the disinfecting power and/or the persistence of the disinfecting effect of antimicrobial substances, comprising the composition according to claim 1.

8. A process for preparing the surfactant composition of claim 1, comprising the successive steps of:
   a) reacting glycine betaine or a salt thereof with a saturated or unsaturated, linear or branched fatty alcohol containing from 8 to 24 carbon atoms, in the presence of an organic or inorganic acid;
   b) cooling the reaction medium to a temperature of from 20 to 90° C.; and
   c) collecting the surfactant composition thus obtained,
   wherein the organic or inorganic acid represents from 1.5 to 2.0 molar equivalents relative to the number of moles of glycine betaine and wherein the reaction is performed at a temperature of from 150 to 180° C.

9. The process according to claim 8, wherein the inorganic acid is selected from the group consisting of: hydrochloric acid, sulfuric acid, perhydrohalic acids, and mixtures thereof and the organic acid is selected from the group consisting of alkylsulfuric acids, arylsulfonic acids, alkylsulfonic acids, and mixtures thereof.

10. The process according to claim 8, wherein the fatty alcohol is selected from the group consisting of: capryl alcohol, decyl alcohol, undecyl alcohol, lauryl alcohol, myristyl alcohol, cetyl alcohol, palmitoleyl alcohol, stearyl alcohol, oleyl alcohol, linoleyl alcohol, linolenyl alcohol, arachidyl alcohol, arachidonyl alcohol, behenyl alcohol, 2-butyloctanol, 2-hexyldecanol, 2-octyldodecanol, 2-decyltetradecanol and mixtures thereof.

11. The process according to claim 8, wherein from 0.8 to 2 equivalents of fatty alcohol, per 1 equivalent of glycine betaine, are used.

12. The process according to claim 8, wherein from 1.5 to 1.9 equivalents of organic or inorganic acid per 1 equivalent of glycine betaine are used.

13. The process according to claim 8, wherein the acid is methanesulfonic acid.

14. The process according to claim 9, wherein perhydrohalic acid is perchloric acid; the alkylsulfuric acid is decylsulfuric acid, laurylsulfuric acid or mixtures thereof; the arylsulfonic acids are selected from benzenesulfonic acid, para-toluenesulfonic acid and mixtures thereof; and the alkylsulfonic acid is selected from triflic acid, methanesulfonic acid, ethanesulfonic acid, decylsulfonic acid, laurylsulfonic acid, camphorsulfonic acid, sulfosuccinic acid, and mixtures thereof.

15. The product according to claim 5, wherein said product is: a cosmetic product; a detergent; a conditioner; or a bituminous emulsion.

\* \* \* \* \*